United States Patent [19]

Hentschel et al.

[11] 4,413,021
[45] Nov. 1, 1983

[54] PROCESS FOR BRINGING LIQUIDS INTO CONTACT

[76] Inventors: Klaus Hentschel, Vosswaldestrasse 5, 6450 Hanua 9; Friedrich Bittner, Mozartstrasse 38, 6232 Bad Soden; Gerd Schreyer, Wildaustrasse 22, 6450 Hanau 9; Georg Franz, Erbstadter Strasse 4, 6369 Niederau 1, all of Fed. Rep. of Germany

[21] Appl. No.: 408,923

[22] Filed: Aug. 17, 1982

Related U.S. Application Data

[62] Division of Ser. No. 94,803, Nov. 15, 1979, Pat. No. 4,377,344.

[30] Foreign Application Priority Data

Nov. 20, 1978 [DE] Fed. Rep. of Germany ....... 2850271

[51] Int. Cl.$^3$ .................... B05D 1/02; B05D 1/34; B05D 7/22
[52] U.S. Cl. .................................. 427/236; 427/426
[58] Field of Search ............................. 427/236, 426

[56] References Cited

U.S. PATENT DOCUMENTS 3,575,880 4/1971 Wojahn et al.
3,794,299 2/1974 Wagner et al.
4,017,413 4/1977 Bittner et al.
4,252,780 2/1981 Koppl et al.

FOREIGN PATENT DOCUMENTS 1670731 12/1970 Fed. Rep. of Germany.
2454910 12/1976 Fed. Rep. of Germany.

OTHER PUBLICATIONS

Ullman, Enzyklopadie der Technishen Chemie, 3rd Edition, 1951, vol. 1, pp. 743–744, 769–770.

*Primary Examiner*—James R. Hoffman
*Attorney, Agent, or Firm*—Cushman, Darby & Cushman

[57] ABSTRACT

There is provided an apparatus for bringing into contact liquids at least one of which is viscous, the apparatus consisting essentially of a tubular container, a first nozzle from introducing a liquid in the upper portion of the container, at least one other nozzle lower than the first nozzle for introducing a different liquid, the tubular container being closeable at the tap thereof and downward from said other nozzle being constricted breast shaped to form a discharge opening, said other nozzles are preferably of polished steel, said other nozzles consist essentially of at least one tangential spray means arranged in at least one row, said other nozzles being slightly above said constriction and being directed in the direction of the upper closeable device or said first nozzle and wherein the discharge opening can discharge into another container which is permanently or detachably connected to the tubular container, said further container can be provided with means for establishing reduced pressure or superatmospheric pressure.

7 Claims, 3 Drawing Figures

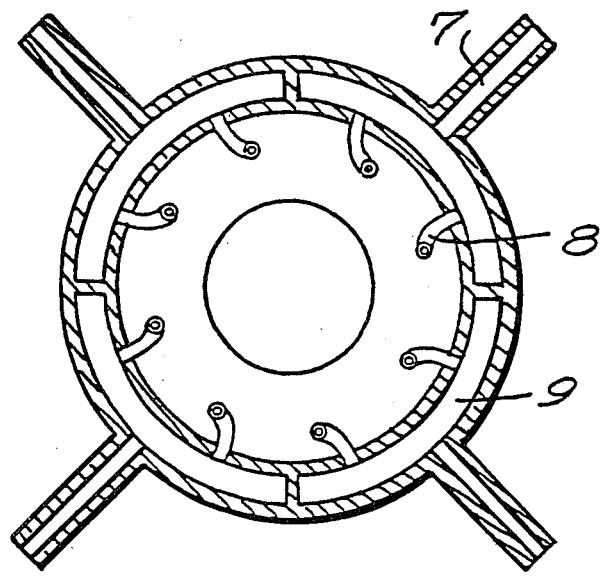
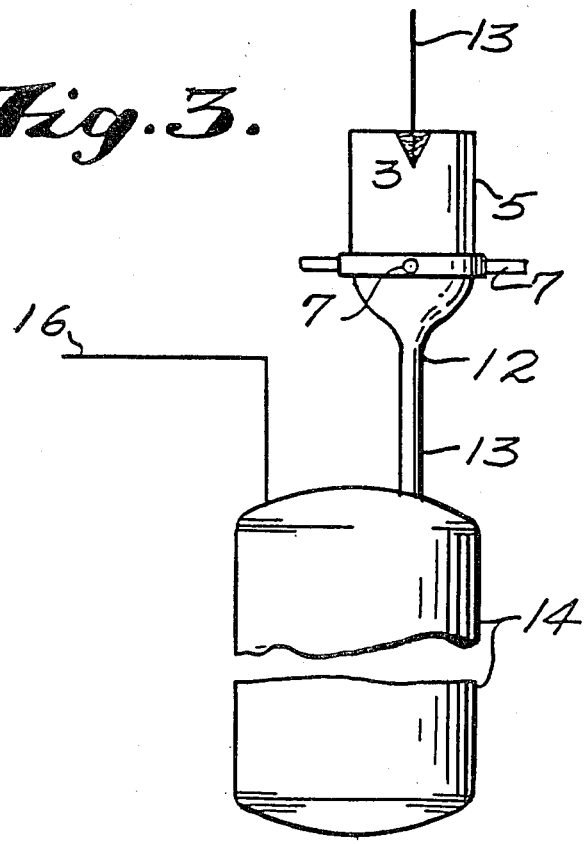

PROCESS FOR BRINGING LIQUIDS INTO CONTACT

This is a division, of application Ser. No. 94,803 filed Nov. 15, 1979 now U.S. Pat. No. 4,377,344.

BACKGROUND OF THE INVENTION

It is known that in an industrial operation the combination of two liquids to form a solution or mixture is only carried out economically with forced turbulently upon turbulent streams (Ullmann, Enzyklopädie der technischen Chemie, 3rd Edition, Vol. 1, 1951 (age 701).

For continuous mixing of liquids above all there are suited quickly running stirring systems or particularly nozzles, in many cases both are even employed simultaneously.

As long as the liquids to be mixed have similar temperatures there usually occur no difficulties. However, if there are brought together different liquids with different temperatures wherein the mixing temperature lies either below the melting point or above the boiling point of a liquid then complications can occur.

If the mixing temperature is above the boiling point of one of the liquids being mixed, i.e. in using a liquified gas then this liquid evaporates up to the saturation point of the solubility. The distribution of a liquified gas in another liquid or liquids is only possible under pressure.

On the contrary if the mixing temperature is below the melting point of a liquid then there exists the danger that this liquid, is using nozzles as the distributor means, becomes solid already at the nozzle orifice. Therefore a fine distribution of the melt in the remaining medium is no longer possible.

Above all this problem occurs in the distribution of viscous liquids in another liquid or in a mixture of liquids, above all, if in so doing simultaneously there occurs a change in condition from liquid to solid.

The mixture of a liquid with a viscous liquid whose melting point lies above the boiling point of the first liquid for the most part has the object of producing small, solid particles of a specific composition with a large surface area.

If the mixing temperature of the suspension formed from the solidified viscous liquid in the other liquid is lower than the boiling point of said other liquid, the solidified molten particles can be separated from the suspension in a simple manner. The viscous liquid added is then present in the form of fine, solid particles.

Thus, e.g., by quenching of metals, salt or sulfur melts with water there are obtained the corresponding powders.

However, it is also possible, with suitable selection of heat withdrawing liquid, depending on the concentration in this liquid to dissolve the solid particles or leave them as a suspension so that it is possible to directly further process them.

Finally with appropriate selection of heat withdrawing liquid or liquids a reaction in the mixing chamber between the viscous material and the liquid or liquids can also take place directly.

As already stated above for the continuous mixing of liquids the use of nozzles is particularly advantageous, even if one of the liquids is viscous. However, with viscous liquids, as stated, there is the danger of solidification occurring too early in leaving the nozzle.

In order to guard against this danger, it is essential that the liquid to be mixed with the sprayed, viscous liquid does not contact the nozzle orifice; however, in spite of this there must be held as small as possible the path of the sprayed liquid until it reaches the other liquid and produce therewith in this manner sprayed particles which are very small.

Of course there are known apparatuses for mixing a melt with a liquid in which the melt is introduced through a nozzle.

However, here the paths between the discharge opening of the nozzle and the reaching of the liquid layer are so long that agglomerates of the crystallizing melt cannot be avoided see for example German Pat. No. 1670731 and related Wojahn U.S. Pat. No. 3,575,880.

In the German patent and Wojahn U.S. patent there is described an apparatus in which molten cyanuric chloride is sprayed into water. The water is introduced tangentially at the upper edge of a mixing container and forms on the side walls of the container a water layer which collects in the lower closed portion and is withdrawn from this lower portion together with the cyanuric chloride suspended in it.

The thus obtained suspension is present in such coarse form that subsequently it must still be comminuted.

The apparatus described also can only be operated at atmospheric pressure.

Additionally there occurs the danger of a clogging of the nozzle in the apparatus described in German OS 2454910 and related Bittner U.S. Pat. No. 4,017,413, in which the liquid layer on the side walls of the mixing tube is only formed below the point of introduction of the melt, entirely apart from the fact that in this case it is not a matter of a true nozzle but of a supply tube for the melt.

SUMMARY OF THE INVENTION

According to the invention there is provided an apparatus which permits the bringing into contact liquids one or more of which can be viscous, with high mixing velocity and below the solidification or setting temperature of the viscous liquid.

This type of apparatus consists essentially of a tubular container with a first nozzle for introducing a liquid, preferably viscous into the upper portion of the container and another nozzle or nozzles lower than the first nozzle for introducing a different liquid or liquids and in which the tubular container is closed or closeable at the top and downward from said other nozzle or nozzles is constricted in breast-shaped form to a discharge opening, said other nozzle or preferably several nozzles are preferably polished steel nozzles, said other nozzles consist essentially of one or more tangentially spray systems arranged in one or more rows which are slightly above the constriction and are directed in the direction of the upper closeable device or the first nozzle and wherein in a given case the discharge opening discharges into another container which is permanently or detachably connected to the tubular container and can be provided with apparatus known in itself for establishing a reduced or superatmospheric pressure.

With this type of apparatus it is possible to so distribute the other liquid or liquids on the chamber wall that the liquid layer is thicker at the breast shaped restriction than at the remainder of the chamber walls.

By the expression used in the glass art: "breast shaped constriction" is meant a constriction which does not proceed steeply, but in a flat S curve going from the wall of the tubular container to the discharge opening. Corresponding constrictions are also present in red wine bottles at the transition from the true bottle to the neck.

The constriction in the tubular container can preferably always begin where about 50% of the sprayed particles meet the liquid layer built up on the wall. Preferably this is the case in the lower third of the tubular container.

The size of the diameter of the discharge opening of itself is not critical. Naturally it depends on the viscosity of the medium being discharged and must have at least such a size that air can enter.

The discharge opening is preferably converted into a discharge tube which has any desired diameter, preferably however, the same diameter or larger than the discharge opening.

The nozzle or nozzles for the water containing organic solvent to be sure can be arranged at any place in the tubular container above the constriction, but preferably are located in the region directly above the breast shaped constriction.

Under "viscous" in the present application there is designated a liquid which is thickly liquid at room temperature. In this expression there also are included the liquids designated as "melts" which are solid at room temperature.

The spraying temperature of the viscous liquid should preferably be in such a range that based on the physical properties of the liquid, "viscosity, surface tension" it permits the formation of the desired finely divided particles. This is ascertained by a preliminary test.

As the tangentially arranged spray agencies, there can be used small tubes or nozzles as well as openings in the chamber walls or, with the presence of a feed ring, in its chamber walls.

BRIEF DESCRIPTION OF THE DRAWINGS

FIG. 2 is a cross-sectional view of the apparatus of FIG. 1; and

FIG. 3 is a schematic view of apparatus for carrying out the invention.

As shown in FIG. 1 the liquid, preferably in viscous form in supply line 1 is led through a coaxial heater 2 via a unary or binary nozzle 3 into the tubular container, i.e. the mixing chamber 5.

Figure 1:
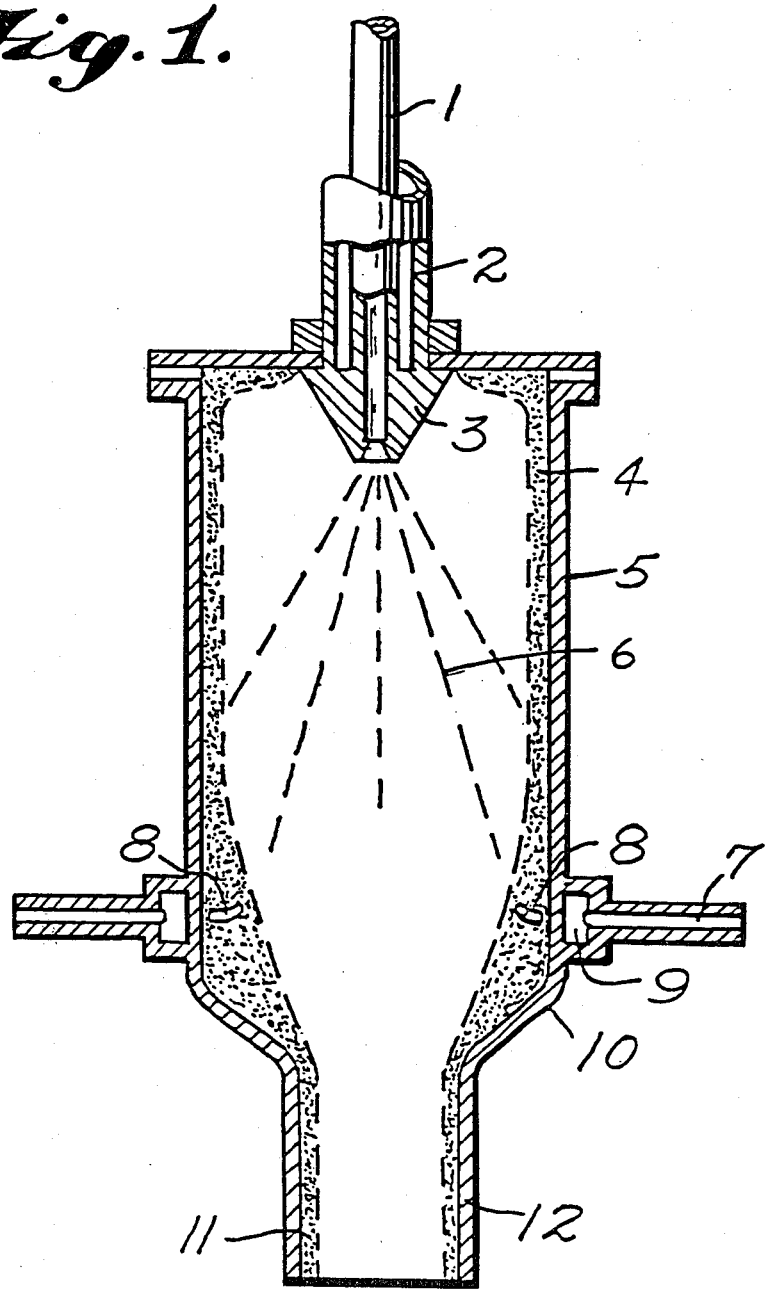
FIG. 1 is a vertical sectional elevation of one form of apparatus suitable for carrying out the process of the invention.

The media being brought into contact with the sprayed material goes through separate supply lines 7 into distribution ring having separate chamber segments 9, see also FIG. 2.

The media is injected tangentially from these chamber segments via the slightly upwardly directed spray systems 8 into the mixing chamber 5.

When using only one supply and only one spray organ, e.g. opening into the mixing chamber 5, the supply 7 passes directly into the spray opening 8 and the segmented chamber 9 is eliminated.

Besides the component in the circumferential direction the solvent jet has a velocity component in the axial direction. Therethrough the liquid reaches the wall of the mixing chamber 5. There is builds a liquid layer 4.

If different solvents are supplied through the supply lines 7, 8 and 9 into the mixing chamber 5, there occurs here an intensive thorough mixing of the supplied liquids, whose intensity can be increased still more by introducing a gas or vapors of the solvent via the spray system 8.

The liquid leaving the nozzle 3 is sprayed into the liquid layer 4. The spray angle for this liquid sprayed out of the nozzles 3 can be between 15 and 150°, preferably between 15 and 120°.

The shape of the spray varies from hollow or solid cone up to an unarranged mist, according to the type of nozzle.

Upon entering the spray particles 6 solidify and/or dissolves in the liquid layer. The energy brought in is given up to the liquid layer, independent of the pressure in the tubular container.

The discharging mixture which leaves the tubular container 5 through the discharge opening 12 goes to the container 14 which can be connected if desired detachably, either directly or indirectly via line 13 to the discharge opening 12 of the container 5.

In this way it is possible to establish any desired pressure, i.e., any reduced or excess pressure, in the tubular container 5 and container 14 through known apparatus which is connected with the container 14 via line 16, see FIG. 3. (However, the known apparatuses for regulating the pressure are not shown in FIG. 3.)

The mixture is withdrawn at the discharge valve 15. The container 14, however, can in a given case also serve as reaction container for a further treatment or reaction.

However, it is also possible to apply reduced or superatmospheric pressure directly into the discharge line 13 through the known apparatuses and to transport away in known manner the discharging mixture from line 13 while eliminating an intermediate connection from container 14.

The apparatuses 5 and 14 shown in FIGS. 1 and 3, in a given case also line 13, can be heated or colled in known manner, according to the requirements, see e.g. Ullmann, Enzyklopädie der technischen Chemie, Vol. 1, 3rd edition, 1951 pages 743–744 and 769–770.

Likewise there can be used for this purpose the known construction materials, loc. cit.

The volume of the tubular container 5 is determined by the properties of the liquid used whereby the path of the sprayed particles 6 up to the impingement on the liquid layer 4 should be held as short as possible.

Through this it is possible to carry out relatively large throughputs in a very small tubular container, e.g. the volume in Example 8 is about 1.2 liters. By establishing a specific pressure, e.g., a reduced pressure in mixing chamber 5, the heat energy of the sprayed component in contact with the liquid layer can be removed. However, the apparatus is also suitable for establishing a superatmospheric pressure if, e.g. gases should be kept in solution. The mixture 11 which leaves the tube 12 can vary and e.g. consist of solid product, liquid and gaseous medium or solution formed from the mixed media and liquid or gaseous product, or of reaction product, liquid and gaseous medium. The number of supply lines 7 depends on the particular case. Thus for the introduction of only a single material one supply line is sufficient, however, for better distribution of this materials there has also proven as desirable to use several supply lines, see for example FIG. 3; even using several components which also can be simultaneously introduced as a mixture the distribution ring described for example in FIG. 2 is suitable.

The exact angle of bending the small tubes in the distribution ring is so regulated depending on the liquid being supplied that the liquid layer reaches exactly the nozzle arranged above in the apparatus, but does not contact the nozzle.

Through the breast shaped constriction and the thicker liquid layer produced at this wall position thereby there results, despite the outlet opening, that the remaining chamber walls always are covered with a uniform, i.e. uninterrupted layer of solvent. Through this there is guaranteed a high mixing velocity.

The apparatus of the invention can be used in many ways.

Thus it is suited for bringing into contact and in a given case reacting liquids of which one liquid can be present as a viscous liquid at the stated contact or reaction temperature, and in a given case one of the components is a liquified gas.

They are very well suited for bringing into contact any type of melt, as, e.g., sulfur, metal or salt melts, with other liquids.

The apparatus is particularly interesting for the production of fine grained particles, e.g., from viscous liquids or mixture of liquids, in solvents, in which there exists the danger that the particle is liable to undergo a chemical change with the solvent in question.

This happens for example in the spraying of liquid cyanuric chloride in solvents which can react with cyanuric chloride.

On the other hand, however, the apparatus of the invention is excellently suited to bring reactable components directly into contact with each other, even if one of these components is present in viscous form, and in a given case one of the components is a liquified gas, or one of the components is present in dissolved form.

This type of carrying out of reactions is especially suitable for reactions in which, as pointed out above, the material injected at the upper end of the apparatus of the invention undergoes change, can be made into solutions or suspensions by the components, introduced at the lower end of the apparatus, as e.g., the hydrolysis of cyanuric chloride.

All of these changes occur as is known through long common residence of the components brought in contact in the contact space.

This danger, however, is not present with the apparatus of the invention since the contact times here are extraordinary short.

Furthermore, very essential is the possibility of employing the apparatus of the invention in reactions in which selectivity is important in which thus there must be avoided further reaction of the reaction product with the other components present or with itself.

Thus e.g., in the reaction of liquid cyanuric chloride with sodium ethyl mercaptide, the formation of the undesired 2,4-dimethylmercapto-6-chloro-s-triazine is greatly reduced.

However, the apparatus of the invention not only is useful for avoiding undesired changes or reactions of the components with each other but also is useful in all cases in which damage can arise through the occurrence of temperature changes.

Since the apparatus of the invention can operate not only under normal pressure but under all pressure, injurious increase in temperature can be compensated for by reducing the pressure and thereby vaporizing a portion of the components.

Besides the particle size can be regulated by selection of the applied pressure and the nozzle here.

Unless otherwise indicated all parts and precentages are by weight.

The process can comprise, consist essentially of or consist of the steps set forth and the materials can comprise, consist essentially of or consist of those set forth. The apparatus can comprise, consist essentially of or consist of the parts set forth.

The invention will be further explained through the following examples.

DESCRIPTION OF THE PREFERRED EMBODIMENTS

EXAMPLE 1

Liquid cyanuric chloride at about 170° C. is led via the heated supply line 1 into the unary nozzle 3. The nozzle 3 has a bore of 1.54 mm and a spray angle of about 78°. The supply pressure of the liquid cyanuric chloride was 5.9 bar. There were sprayed 80.5 kg/h of cyanuric chloride through the nozzle 3 into the mixing chamber 5. The mixing chamber 5 had a diameter of 100 mm and atmospheric pressure prevailed in it. Water (966 kg/h) via 4 different supply lines 7 arrived at the chamber segments 9 and after leaving from light small tubes 8 formed a liquid layer 4 in the mixing chamber 5.

The suspension of cyanuric chloride and water left the mixing chamber 5 through the pipe 12. The concentration of cyanuric chloride in the suspension was 7.7%.

The value of the Simazin test, (see Ullmann, Enzyklopädie der technischen Chemie, 4th edition, 1975, Vol. 9, page 652), a measure for the reactability of cyanuric chloride was 55 min, and 0.6% residue. The ASS test (Ullmann, Vol. 9, page 652) produced a residue of 0.6%.

EXAMPLE 2

The experimental conditions were changed compared to Example 1 as follows:

The bore of the cyanuric chloride nozzle 1.1 mm
The spray supply pressure 6.0 bar
The amount of cyanuric chloride 40.5 kg/h
The pressure in the mixing chamber 0.13 bar and the resulting cyanuric chloride concentration in water was 4.0%.

The value of the Simazin test was 55 min. and 0.2% residue. The ASS test produced a residue of 0.5%.

EXAMPLE 3

The experimental conditions were changed compared to Example 1 as follows:

The bore of the cyanuric chloride nozzle 1.85 mm.
The spray supply pressure 6.0 bar.
The amount of cyanuric chloride 118 kg/h.
and the resulting cyanuric chloride concentration in water was 10.9%.

The value of the Simazin test ws 45 min. and 0% residue. The ASS test produced a residue of 0.3%.

EXAMPLE 4

The experimental conditions were changed compared to Example 1 as follows:

The bore of the cyanuric chloride nozzle 1.17 mm.
The spray angle of the nozzle about 70°.
The amount of cyanuric chloride 30.6 kg/h.
The amount of water 555 kg/h.
The chamber diameter 80 min.

and the resulting cyanuric chloride concentration in water was 5.2%.

The value of the Simazin test was 37 min. and 0% residue. The ASS test produced no residue.

The particle spectrum of the cyanuric chloride particles produced in Example 1-4 on the average had the following appearance.
>100 microns 3%
>63 microns 14%
>40 microns 33%
>10 microns 50%
<10 microns 50%

EXAMPLE 5

The experimental conditions were changed compared to Example 1 as follows:
The bore of the cyanuric chloride nozzle 2.6 mm.
The spray supply pressure 4.5 bar
The amount of cyanuric chloride 340 kg/h
The amount of acetone 1100 liters/h
The water content in the acetone 2%
The pressure in the mixing chamber 0.13 bar
and the resulting cyanuric chloride concentration in the acetone was 28.4%. The temperature of the discharging suspension was 14° C. The degree of hydrolysis of the cyanuric chloride after the mixture stood for 1 hour was 0.3%. The photographically determined particle spectrum showed no particles greater than 100 microns.

EXAMPLE 6

Liquid sulfur having a temperature of about 150° C. was led via the heated supply line 1 into the unary nozzle 3. The nozzle has a spray angle of about 90°. The pressure of supply of the melt was 7.2 bar. There were sprayed 62.5 kg/h of sulfur through the nozzle into the mixing chamber 5. The mixing chamber 5 had a diameter of 100 mm and atmospheric pressure prevailed in it.

Toluene (1070 kg/h) reached the chamber segments 9 via four different supply lines 7 and after emerging from the eight small tubes 8 formed a liquid layer 4 in the mixing chamber 5.

The sulfur-toluene suspension left the mixing chamber 5 via the tube 12. Its concentration of sulfur was 5.5%.

EXAMPLE 7

Liquid sodium having a temperature of about 120° C. was led via the heated supply line 1 into the unary nozzle 3. The nozzle had a spray angle of about 78°. The applied pressure of the melt was 4.2 bar. There were sprayed through the nozzle 57 kg/h of sodium into the mixing space 5. The mixing chamber 5 had a diameter of 80 mm and atmospheric pressure prevailed in it.

Diethyl ether (540 kg/h) reached the chamber segments 9 via three different supply lines 7 and after emerging from the six small tubes 8 formed a liquid layer 4 in the mixing chamber 5. To render the mixture inert there were led through four supply lines 7300 l/h of nitrogen into the mixing chamber 5.

The sodium and ether suspension left the mixing chamber 5 through the tube 12 at a sodium concentration of 9.5%.

EXAMPLE 8

Liquid cyanuric chloride at about 165° C. was led via the heated supply line 1 into the unary nozzle 3. This nozzle 3 has a bore of 2.6 mm and spray angle of about 90°. The supply pressure of the melts was 6.5 bar. There were sprayed 320 kg/h of liquid cyanuric chloride through the nozzle 3 into the mixing chamber 5. This mixing chamber 5 has a diameter of 100 mm, the pressure of the mixing chamber was 0.13 bar.

1070 liters/h of toluene via four different supply lines 7 arrived at the chamber segments 9 and after leaving from eight small tubes 8 formed a liquid layer 4 in the mixing chamber 5.

the suspension of cyanuric chloride left the mixing chamber 5 through the pipe 12. The concentration of cyanuric chloride in the suspension was 25.7%.

The particle spectrum determined photographically showed 90% of the particles below 10 microns.

EXAMPLE 9

Liquid cyanuric chloride at about 170° C. was led via the heated supply line 1 into the unary nozzle 3. The nozzle had a bore of 0.8 mm and a spray angle of about 78°. The supply pressure of the melt was 4 bar. There were sprayed through the nozzle 44.7 kg/h of cyanuric chloride into the mixing chamber 5. The mixing chamber 5 had a diameter of 80 mm and atmospheric pressure prevailed in it.

Methylene chloride in an amount of 364 liters/h via two opposed supply lines 7 via four small tubes 8 reached the mixing chamber 5 and through a differed supply line 7, 9.7 kg/h of sodium hydroxide dissolved in 100 liters of water reached the mixing chamber and through four supply lines 7 there were introduced into the mixing chamber 20.5 kg/h of an isopropylamine solution which contained 70 weight % of isopropylamine.

The 2-isopropylamino-4,6-dichloro-s-triazine was isolated from the discharging reaction mixture with yield of more than 99%. According to a thin layer chromatogram the product was homogeneous.

(DC-running agent consisted of 14 parts by weight of petroleum ether 50/75, one part by weight ethyl acetate, 2 parts by weight of chloroform and 2 parts by weight of glacial acetic acid.)

EXAMPLE 10

Liquid cyanuric chloride at about 170° C. was led via the heated supply line 1 into the unary nozzle 3. The nozzle had a bore of 0.8 mm and a spray angle of about 78°. The supply pressure of the melt was 6 bar. There were sprayed 49 kg/h of liquid cyanuric chloride through the nozzle 3 into the mixing chamber 5. The mixing chamber 5 had a diameter of 80 mm and a pressure of 4 bar prevailed in it.

Liquid-n-butane in an amount of 610 liters/h through four opposed supply lines 7 via eight small tubes 8 reached the mixing chamber 5.

The discharging mixture passed into an intermediate container. From this intermediate container it was conveyed into an expansion container where the n-butane vaporized at a pressure of 0.1 bar. The powdery cyanuric chloride remaining behind had a particle size of more than 95% below 100 microns.

The entire disclosure of German priority application P 28 50 271.8-23 is hereby incorporated by reference.

What is claimed is:

1. A process for the production of a suspension or solution by mixing a plurality of liquids at least one of which is a viscous liquid comprising providing an apparatus comprising a tubular container having a first spray nozzle means in the upper portion of the container and at least one other nozzle means in the form of tangential spray means lower than said first spray nozzle means, said tubular container being closeable at the top and being constricted in breast shaped manner slightly downwardly from said other nozzle means to form a discharge opening, said constriction being in the form of a flat S curve going from the wall of the tubular container to the discharge opening, introducing the viscous liquid through said first spray nozzle means into the container, spraying at least one other liquid through said other tangential nozzle means and into said tubular container in the direction of said first spray nozzle means to form a liquid layer on the wall of the container which is thickest in the region of the breast shaped constriction.

2. The process of claim 1 wherein the viscous liquid is sprayed into the container.

3. The process of claim 2 wherein said other nozzle means are located directly above the breast shaped constriction.

4. A process according to claim 1, wherein the viscous liquid is sulfur.

5. A process according to claim 4, wherein the other liquid is toluene.

6. A process according to claim 1, wherein the viscous liquid is sodium.

7. A process according to claim 5, wherein the other liquid is diethyl ether.

* * * * *